United States Patent [19]

Smith

[11] Patent Number: 4,839,289

[45] Date of Patent: Jun. 13, 1989

[54] MONOCLONAL ANTIBODIES TO A BROAD RANGE OF MAMMALIAN TERMINAL DEOXYNUCLEOTIDYL TRANSFERASES

[75] Inventor: R. Graham Smith, Dallas, Tex.

[73] Assignee: The Board of Regents of the University of Texas System, Austin, Tex.

[21] Appl. No.: 802,039

[22] Filed: Nov. 26, 1985

[51] Int. Cl.$^4$ .............................................. C12N 5/00
[52] U.S. Cl. .............................. 435/240.27; 530/387; 530/808, 530/809; 435/172.2; 435/68
[58] Field of Search ......................... 435/240.27, 172.2; 530/387, 808, 809, 68

[56] References Cited

PUBLICATIONS

Augl, et al, Fed. Proc. 42: 2147, 1983.
Bollum, F. J. et al, J. Bio. Chem 259: 5848, 1984.
Sasaki, R. et al, Igaku no Ayum vol. 134(4), 1985, pp. 185–186.
Fuller, S. A. et al, Biochem J. (1985) 231, 105–113.

*Primary Examiner*—Christine M. Nucker
*Assistant Examiner*—Karen I. Krupen
*Attorney, Agent, or Firm*—Myron C. Cass

[57] ABSTRACT

Murine monoclonal antibodies specific to unique antigenic determinants on mammalian terminal deoxynucleotidyl transferases (TdT). The monoclonal antibodies specifically bind to TdT in a wide variety of mammalian cells including human, mouse, rat, rabbit and bovine origin. The monoclonal antibodies are secreted by hybridoma cells derived from fusion of murine plasmacytoma cells with splenocytes from mice immunized with TdT from bovine thymus cells. The monoclonal antibodies can detect small numbers of TdT-positive cells for monitoring of TdT-positive leukemias and lymphomas in multiple species, including human.

2 Claims, 1 Drawing Sheet

MONOCLONAL ANTIBODIES TO A BROAD RANGE OF MAMMALIAN TERMINAL DEOXYNUCLEOTIDYL TRANSFERASES

BACKGROUND OF THE INVENTION

This invention relates to murine monoclonal antibodies and particularly relates to production of unique monoclonal antibodies which specifically bind to terminal deoxynucleotidyl transferase (TdT) enzyme in lymphocyte cells of a variety of mammals, including humans.

Although TdT is found in a very small percentage of normal lymphoblasts, particularly in the early development of the immune system of vertebrates, elevated levels of TdT have been used in the diagnosis of human leukemias. TdT has become a valuable enzymatic marker for lymphoblastic neoplasms, such as acute lymphoblastic leukemia (ALL), chronic granulocytic leukemia (CGL) and lymphoblastic lymphoma (LL). Consequently, research has been conducted to develop methods for measurement of the frequency of lymphocytes which are positive for TdT in both normal and leukemic mammals. U.S. Pat. No. 4,307,189 describes a method for quantitative determination of TdT using labelled deoxynucleoside triphosphates which are converted by TdT to fluorescent or radioactive polydeoxynucleotides which may be quantified as a reflection of the amount of TdT originally present in the biological sample. However, this method does not employ monoclonal antibodies to TdT.

In studies published by C. Augl et al (Fed.-Proc.42:2147 1983) (Abstract) the production of monoclonal antibodies to bovine TdT has been reported without description of detailed binding recognition of the antibodies. Immunochemical studies of TdT in a variety of mammals have demonstrated that peptides of this enzyme are immunologically related when probed with antiserum prepared to the degraded enzyme from bovine thymus as reported by F. J. Bollum (Journal of Biological Chemistry 256:8768, 1981).

In studies published by F. J. Bollum, et al. (Journal of Biological Chemistry 259: 5848 1984), the production of monoclonal antibodies to human TdT has been described. These anti-human monoclonal antibodies were widely variable in ability to recognize epitopes or determinants on TdT in human and calf cells.

SUMMARY OF THE INVENTION

Murine monoclonal antibodies specific to a unique antigenic determinant or epitope of TdT are produced. These monoclonal antibodies sepcifically recognize TdT in a wide variety of mammalian cells, including human, mouse, rat, rabbit and bovine origin. Three particular antibodies cross-react with the same epitope on TdT, and a fourth particular monoclonal antibody reacts with a distinct epitope, as determined by competitive displacement assay. The monoclonal antibodies reactively bind to human and calf TdT, as well as extracts of rabbit, mouse and rat thymus which contain TdT-positive cells; they do not reactively bind to murine spleen which does not contain TdT-positive cells.

The monoclonal antibodies are secured by new hybridoma cell lines derived from fusion of murine plasmacytoma cells with splenocytes from mice immunized with TdT from bovine thymus cells.

By reason of their specificity, these monoclonal antibodies are useful in characterizing the conserved regions common to TdT enzymes in a variety of mammals. The ability of fluorochrome-conjugated derivatives of these monoclonal antibodies to detect small numbers of TdT-positive cells by flow cytometry technique is particularly useful for analysis of developing lymphocytes and for monitoring of TdT-positive leukemias and lymphomas in multiple species, including human.

DESCRIPTION OF THE SPECIFIC EMBODIMENTS

Figure 1:
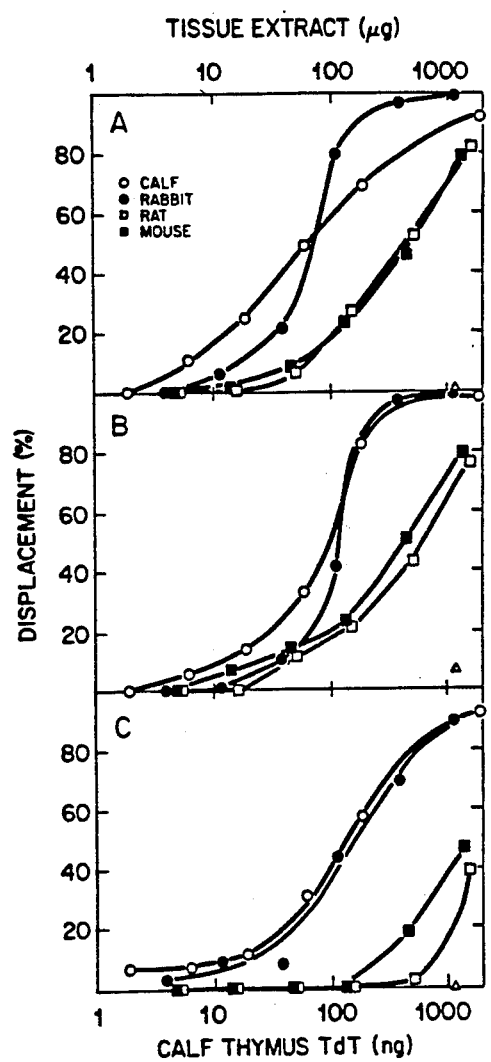
FIG. 1 is a combined comparative graph showing separate competitive displacement assays for three monoclonal antibodies of the invention from immobilized bovine TdT by soluble calf TdT and extracts of rabbit, mouse, and rat thymus.

This invention provides murine monoclonal antibodies specific to unique antigenic determinants of TdT on normal and neoplastic mammalian cells. Embodiments of hybrid cells or hybridomas capable of producing monoclonal antibodies to a broad range of TdT-positive cells were prepared as follows:

Immunization Protocol: Ten female Balb/c mice, 5 weeks of age, were immunized with 15–25 $\mu$g of purified TdT crosslinked with glutaraldehyde and emulsified with an equal volume of Freund's complete adjuvant. TdT was purified from bovine thymus by a minor modification of the procedure of Chang and Bollum (J. Biol.Chem.246:909, 1971). Analysis of the reduced final (hydroxyapatite) fraction on polyacrylamide gels containing sodium dodecyl sulfate revealed major peptides of estimated Mr 43,000, 32,000, and 10,000. The emulsion was divided into 4 equal parts and injected subcutaneously into axillary and inguinal regions. For the first fusion, mice were immunized three times at intervals of 4 weeks. All immunizations after the second contained incomplete Freund's adjuvant. Mice were bled 5 days after the third immunization and the sera were tested for antibodies to TdT in two ways. First, sera were diluted and tested for inhibition of the enzymatic activity of TdT. Inhibition of the enzymatic activity of TdT was assayed by mixing dilutions of sera in 10 mM KPO$_4$, 150 mM NaCl pH 7.4 (PBS), and 10 mg/ml bovine serum albumin (PBA) with purified enzyme (about 0.3 unit) for one hour at 25° C. Standard assay conditions were then established; one unit of enzymatic activity equals 1 nM dGTP incorporated/hr at 37° C. Negative controls were normal mouse serum and purified MOPC 21 IgG$_1$. Second, dilutions of sera were tested by indirect immunofluorescence for binding to the nuclei of the TdT-positive pre B cell line NALM-6 from a human donor with acute lymphoblastic leukemia (ALL). Sera were also tested in the same way on the TdT-negative normal human B lymphoblastoid cell line RPMI 1788 containing EBV. On the basis of these tests, one animal was selected for hyperimmunization prior to sacrifice and splenectomy. Two weeks after the third subcutaneous immunization, a series of intraperitoneal inoculations with untreated TdT were given to this mouse; on days 6, 4, 3, 2 and 1 prior to splenectomy, 7.5, 25, 62, 62, and 62 $\mu$g were injected intraperitoneally without adjuvant. One day after the final injection, the spleen was removed for cell fusion.

Fusion: Splenocytes were fused to SP2/0 murine plasmacytoma cells with minor modifications of the optimum conditions of Fazekas de St. Groth et al (J.Immunol. Methods 35:1, 1980). Splenocytes and plasmacytoma cells were mixed at a ratio of 4:5.

Screening: Hybridoma supernatants were tested by indirect immunofluorescence for reactivity with the nuclei of the TdT-positive NALM-6 cells. Positive supernatants were tested for reactivity with the RPMI 1788 cells, a TdT-negative line. Hybridomas which produced antibodies reactive with NALM-6 but not RPMI 1788 cells were retained for further characterization. Feathery nuclear staining which spared condensed metaphase chromosomes and was absent in RPMI 1788 cells characterized specific reactions. Certain nonspecific binding patterns, common to both NALM-6 and RPMI 1788 cells, included cytoplasmic, chromosomal, and pancellular staining reactions. Hybridomas producing such antibodies were discarded.

This fusion yielded 449 hybridomas, 3 of which produced antibodies reactive with NALM-6 and not RPMI 1788 cells. These hybridomas were cloned by limiting dilution and two of these hybridomas were unstable upon cloning. The remaining hybridoma, designated "TdT4 hybridomas" secreted an $IgG_1$ immunoglobulin, the monoclonal antibody designated "TdT4".

After a rest period of 4.5 months, immunization of the remaining 9 mice was resumed at monthly intervals with crosslinked TdT emulsified in incomplete Freund's adjuvant. At periodic intervals, the mouse sera were tested in the immunofluorescence and enzyme inhibition assays and, after the eighth immunization, one mouse was selected for hyper-immunization. Beginning one week after the final subcutaneous immunization, this animal received 25, 50, 50, 50 and 50 μg of native TdT intraperitoneally on days 7, 4, 3, 2 and 1 prior to splenectomy.

Fusion of the splenocytes was performed by the method of the previously described fusion of splenocytes with SP2/0 murine plasmacytoma cells.

A total of 524 hybridomas resulted, four of which were selected for further characterization based on differential staining of NALM-6 cells. Three of these four hybridomas were stable after cloning and are designated "TdT1, TdT2 and TdT3 hybridomas"; all three secreted $IgG_1$ immunoglobulins, the respective monoclonal antibodies designated "TdT1, TdT2 and TdT3".

Samples of the four hybridomas which secrete the respective monoclonal antibodies are deposited with the American Type Culture Collection (ATCC) namely HB 9178 (TdT1), HB 9179 (TdT2), HB 9180 (TdT3 and HB 9181 (TdT4).

Immunoprecipitation: Since the antibodies were selected on the basis of immunofluorescence reactivity with cultured human TdT positive NALM-6 cells, extracts of the same cells metabolically labeled with [$^{35}$S]-methionine were analyzed by immunoprecipitation. NALM-6 cells ($10^7$) were washed and incubated in 10 ml methionine-free RPMI 1640 medium containing 10% dialyzed fetal bovine serum for one hour at 37° C. [$^{35}$S]-methionine (100 uCi/ml) (sp. act. 1140 Ci/ml, Amersham, Arlington Heights, IL) was added and the cells incubated for 4 hours. After washing, cells were lysed in 2 ml 13 mM tris HCl pH 7.4, 21 mM $MgCl_2$, 300 mM KCl, 0.5% Triton X-100, 1 mM phenylmethylsulfonyl fluoride, and 100 kallekrein inhibitory units/ml aprotinin. After centrifugation at 100,000 xg for 30 minutes, the extract was incubated with 400 μl Cowan A strain S. aureus suspension (SAS) treated with 40 μl rabbit anti-mouse IgG (Pel-Freeze Biologicals, Rogers AK) and 4 μg MOPC 21 $IgG_1$. After centrifugation, the extract was incubated with 400 μl untreated S. aureus suspension. In some experiments, the extract was treated a third time with SAS in a manner identical to the first treatment. Aliquots of 100 μl of extract (about $10^7$ CPM) were incubated with either 50 μl of a 1/100 dilution of ascites fluid, 1 mg/ml purified MOPC-21 $IgG_1$, rabbit anti-TdT heteroantiserum or normal rabbit serum for 1 hour at 4° C. Rabbit anti-mouse IgG (5 μl) was added for 1 hour to all samples containing mouse antibodies SAS (25 μl) was added and washed 4 times with 0.05 M tris-Cl pH 8.0. 0.5 M NaCl, 0.5% NP-40, 0.2% sodium deoxycholate, and 0.1% sodium dodecyl sulfate (SDS). The pellets were then resuspended in 50 μl of 10 mM tris-Cl, 140 mM 2-mercaptoethanol, 0.5% SDS 0.25 M sucrose, 0.002% bromophenol blue, pH 8.0, boiled for 3 minutes, and electrophoresed through 10% polyacrylamide gels containing SDS according to Laemmli et al (Nature 227:680,1970). Fluorograms were prepared in the method as described by W.M. Bonner et al (Eur. J. Biochem. 46:83, 1974). All 4 monoclonal antibodies, as well as a rabbit heteroantiserum to TdT, specifically immunoprecipitated a peptide of Mr 60,000 daltons from such extracts. Previous work has demonstrated that heteroantisera to TdT immunoprecipitate a single polypeptide of Mr 60,000 daltons from cultured lymphoblasts.

Reactivity of Antibodies with Proteolytic Fragments of Bovine TdT: To determine whether these antibodies react with similar or distinct epitopes on the TdT molecule, bovine TdT was partially digested with S. aureus V8 protease in the presence of 125 mM tris-Cl pH 6.8, 10% SDS and 100 mM EDTA as described by Cleveland (Methods Enzymol 96:222, 1983). Untreated enzyme or enzyme containing 60, 90, and 120 μg/ml V8 protease was incubated at 37° for 30 minutes. Samples were adjusted to 5% 2-mercaptoethanol and 2% SDS, boiled for 2 minutes, ane electrophoresed through a 17.5% Laemmli SDS-polyacrylamide gel. The peptides and molecular weight markers were electrophoretically transferred to 0.1 micron pore size nitrocellulose paper as described by Towbin et al (Proc Natl Acad Sci USA 76:4350, 1979). After blocking with 0.05% Tween-20 in PBS, the paper strips were treated with 1 μg/ml purified monoclonal antibody TdT1, TdT2, TdT3, or TdT4; MOPC-21 IgG1 was used as a control. After washing, the strips were developed with horseradish peroxidase-conjugated goat anti-rabbit IgG followed by peroxidase-conjugated rabbit anti-goat IgG. The enzyme fragments which had bound the monoclonal antibodies were then visualized by incubation with 4-chloro, 1-naphthol in the presence of hydrogen peroxide.

Antibodies TdT1, 2, and 3 each reacted with 2 peptides of estimated molecular weights 43,800 and 11,000 in preparations of undigested bovine TdT. Antibody TdT4 reacted with the larger of these peptides, but staining was faint. In partial digests prepared with 60 μg/ml protease, antibody TdT1 bound to the same 14 peptides as did TdT2. These peptides ranged in size from 43,800 to 9,000. Antibody TdT3 bound to 9 of these same 14 peptides. These 9 peptides are of estimated Mr 43,800; 42,800; 37,700; 36,600; 35,600; 34,700; 32,600; 31,500; and 29,900. One peptide of Mr 18,000 which was faintly stained by antibodies TdT1 and 2 was not recognized by antibody TdT3. Due to the fainter staining of certain peptides by antibody TdT3, it is difficult to interpret its lack of binding to 5 other peptides bound by both TdT1 and 2. These results are currently interpreted as suggesting that antibodies TdT1, 2, and 3 bind to the same determinant on the bovine TdT molecule.

In similar immunoblotting experiments, antibodies TdT1, 2, and 3 specifically bound to a peptide of Mr 60,000 derived from extracts of cultured human cell lines which contain enzymatically active TdT (NALL-1, NALM-6, RPMI 8402, and REH). This peptide was not found in immunoblots derived from extracts of human cell lines which do not contain enzymatically active TdT (Daudi, RPMI 8392, and RPMI 1788).

Cross-reactivity of Antibodies: To assess whether these 4 antibodies recognize similar or distinct epitopes on the TdT molecule, unconjugated antibodies were tested for their ability to displace the binding of [$^{125}$I]-labeled antibodies to immobilized bovine TdT. Antibodies were purified from ascites fluid using Affi-Gel protein A (Bio-Rad Laboratories, Richmond, CA). Antibodies TdT1, 2 and 3 displaced each other in these competition assays, suggesting cross-reactivity with identical or sterically closely spaced determinants. Unconjugated TdT1 and 2 fully displaced [$^{125}$I]-TdT1, 2 and 3, while displacement [$^{125}$I]-TdT1 and 2 by TdT3 was incomplete at the highest input of unconjugated antibody. TdT4 clearly bound to determinants distinct from those recognized by TdT1, 2 and 3, since the former antibody did not compete with the latter 3 for binding to calf TdT in any mixture of conjugated and unconjugated antibodies.

Extracts of thymus were tested in competitive radioimmunoassay to assess the cross-reactivity of antibodies TdT1, 2 and 3 with mouse, rat, rabbit, and purified bovine TdT. As illustrated in FIG. 1, each of the thymic extracts displaced all 3 antibodies from immobilized bovine TdT. The general contour and extent of the displacement obtained with bovine TdT and the rabbit thymus extract was similar, suggesting dose similarity of the involved antigenic determinants as recognized by these antibodies. The degree of displacement was less complete with mouse and rat extracts than with the rabbit extract, particularly with antibody TdT3. The specific activity of TdT in the murine extract was lower than in the other extracts. However, the cross-reactivity of the rat enzyme with all 3 antibodies appeared to be of a lower order than that of the rabbit enzyme. An extract prepared from murine spleen, which did not contain TdT-positive cells, did not compete for binding to any of the monoclonal antibodies. These results clearly show that antibodies TdT1, 2 and 3 bind mouse, rat, rabbit, and human, in addition to bovine, TdT, while antibody TdT4 binds at least the human and bovine enzymes. The inefficient displacement of antibody TdT4 by soluble enzyme precluded testing with the thymic extracts.

In FIG. 1, A is antibody TdT1; B, TdT2; C, TdT3. The specific activities of TdT in the rabbit, mouse and rat extracts were 3.6, 0.78, and 4.9 U/mg, respectively. The displacement by an extract of murine spleen (Δ) is shown at the lower right corner of each panel.

Additional extracts of cell line and tissues were tested for their ability to displace the binding of [$^{125}$I]-conjugated antibodies to immobilized calf TdT in competitive radioimmunoassays. Only the ALL cell lines known to contain enzymatically active TdT yielded extracts that efficiently displaced these antibodies. Extracts prepared from the promyelocytic cell line HL-60 and the B cell lines Daudi and RPMI 1788 did not compete for antibody binding.

Enzyme inhibition assay: Inhibition of the enzymatic activity of TdT was assayed by mixing dilutions of purified antibodies in 10 mM KPO$_4$, 150 mM NaCl pH 7.4 (PBS), and 10 mg/ml bovine serum albumin (PBA) with purified enzyme (about 0.3 unit) for one hour at 25° C. Standard assay conditions were then established; one unit of enzymatic activity equals 1 nM dGTP incorporated/hr at 37° C. Negative controls were normal mouse serum and purified MOPC 21 IgG$_1$. Antibodies TdT1, 2 and 3 each inhibited the catalytic activity of bovine TdT, although inhibition was incomplete even in the presence of approximately a 7-fold molar excess of antibody. Inhibition by antibody TdT4 was minimal even at the highest input tested. None of these antibodies inhibited the activity of calf thymus DNA polymerase.

Specificity of Antibodies: Immunofluorescence: Various cultured and fresh human leukocytes whose contents of TdT were measured enzymatically were assayed for TdT immunoreactivity by indirect immunofluorescence. Cells were pelleted onto slides fixed, stained and detected with fluorescein isothiocyanate (FITC) conjugated sheep anti-mouse IgG supplied by Cappel Laboratories of Malvern, PA. The fractions of cells stained with each of the 4 monoclonal antibodies and a well-characterized rabbit heteroantiserum C537 were compared. All 4 cell lines known to contain large amounts of enzymatically active TdT were stained to the same extent by each of the monoclonal antibodies and by the rabbit antiserum as summarized in Table 1. Four of five lines in which the enzymatic activity of TdT was undetectable were not stained by any of these antibodies. A small fraction (2-6%) of cells of the pre-B ALL line SMS-SB were stained by the monoclonal antibodies as well as the rabbit heteroantiserum. This cell line is known to express a small minority of TdT-positive cells detectable by immunofluorescence but not by enzymatic assay under standard conditions of assay sensitivity.

TABLE 1

Immunofluorescence Staining of Cultured Human Hemopoietic Cell Lines for TdT

| Cells | Phenotype | Enzymatic Activity (units/10$^8$ Cells) | Antibodies | | | | |
|---|---|---|---|---|---|---|---|
| | | | TdT1 | TdT2 | TdT3 | TdT4 | C537 |
| | | | Stained Cells (% of total) | | | | |
| REH | ALL | 65 | 99 | 96 | 99 | 95 | 97 |
| NALM-6 | ALL | 44 | 91 | 90 | 95 | 95 | 91 |
| NALL-1 | ALL | 40 | 99 | 99 | 99 | 95 | 99 |
| RPMI 8402 | T-ALL | 56 | 99 | 95 | 95 | 95 | 99 |
| SMS-SB | ALL | <10 | 4 | 4 | 2 | 6 | 2 |
| HL-60 | AML | <10 | <0.1 | <0.1 | <0.1 | <0.1 | <0.1 |
| Daudi | Burkitt's | <10 | <0.1 | <0.1 | <0.1 | <0.1 | <0.1 |

TABLE 1-continued

Immunofluorescence Staining of Cultured
Human Hemopoietic Cell Lines for TdT

| Cells | Phenotype | Enzymatic Activity (units/$10^8$ Cells) | Antibodies | | | | |
|---|---|---|---|---|---|---|---|
| | | | TdT1 | TdT2 | TdT3 | TdT4 | C537 |
| | | | Stained Cells (% of total) | | | | |
| RPMI 8392 | B Lymphoblastoid | <10 | <0.1 | <0.1 | <0.1 | <0.1 | <0.1 |
| RPMI 1788 | B Lymphoblastoid | <10 | <0.1 | <0.1 | <0.1 | <0.1 | <0.1 |

The sensitivity of the enzyme assay was 10 units/$10^8$ cells. Abbreviations: ALL, acute lymphoblastic leukemia; T-ALL, T cell ALL; AML, acute myelogenous leukemia.

Additionally leukocytes from the blood of patients with various leukemias were tested by indirect immunofluorescence, and all 4 monoclonal antibodies stained only those cells that contained enzymatically active TdT. These leukemias included acute lymphoblastic leukemia (4 patients), chronic granulocytic leukemia in lymphoblastic transformation (1 patient), acute myelogenous leukemia (2 patients), and chronic lymphocytic leukemia (3 patients). Antibodies TdT1, 2 and 3 stained the same fraction of cells as did the rabbit antiserum. Antibody TdT4 stained a slightly smaller fraction of some cell populations than did the other antibodies. All 4 antibodies stained 99% of chronic granulocytic leukemia in lymphoblastic transformation (GL) cells, which expressed a very high amount of enzymatically active TdT.

Flow Cytometry: For direct immunofluorescence, purified monoclonal antibodies were conjugated with FITC as described by Goding in "Immunofluorescence" (Chapter 7) in *Monoclonal Antibodies: Principles and Practice*, New York, Academic Press, 1983 p. 227. Mixtures of TdT-positive NALM-6 and TdT-negative RPMI 1788 cells were fixed in 4% paraformaldehyde in 10 mM KPO$_4$, 150 mM NaCl, pH 7.4 (PBS). The cell mixtures included 0, 1, 3, 10, 30, and 100% NALM-6 cells with 100%, 99%, 97%, 90%, 70% and 0% RPMI 1788 cells. Cells were then fixed in a sequence of 50%, 100%, and finally, 50% acetone solutions in water at 0° C. The cells were washed in PBS containing 10 mg/ml bovine serum albumin and 0.1% NaN$_3$ (PBA). Fixed cells ($10^6$) were incubated in normal mouse serum for 10 minutes and then incubated 12 hours at room temperature with a 1/32 dilution in 100 μl mouse serum of a mixture of equal amounts of FITC-conjugated monoclonal antibodies TdT1, 2, 3 and 4. The final antibody protein concentration was 13 μg/ml. The stained cells were washed twice with PBA, fixed with 4% paraformaldehyde, washed with PBA, and analyzed on an Ortho 50H cytofluorograph. As negative controls, NALM-6 cells were stained with either FITC-goat anti-rabbit IgG 1/40 dilution in mouse serum or with FITC-MOPC 21 IgG1. The staining of both NALM-6 and RPMI 1788 cells was unimodal, with broad separation of mean fluorescence channels obtained with the TdT-positive and negative cells. The fraction of TdT-positive cells detected by flow cytometry agreed closely with the measured fraction of NALM-6 cells mixed with RPMI 1788 cells.

I claim:

1. A hybrid cell line derived from murine genus which produces a monoclonal antibody which specifically binds to an epitope on terminal deoxynucleotidyl transferase (TdT) derived from a group of mammalian cells consisting of cells of human, mouse, rat, rabbit and bovine origin; said cell lines on deposit with the American Type Culture Collection having A.T.C.C. deposit numbers HB 9178 (TdT1), HB 9179 (TdT2) and HB 9180 (TdT3).

2. A monoclonal antibody produced by any one of the hybrid cell lines of claim 1.

* * * * *